United States Patent [19]

Gandolfi

[11] Patent Number: 4,614,811
[45] Date of Patent: Sep. 30, 1986

[54] NOVEL ORGANOPLATINUM(II) COMPLEXES AND METHOD FOR THE PREPARATION THEREOF

[75] Inventor: Ottavio Gandolfi, Rome, Italy

[73] Assignee: Yissum Research Development Company of the Hebrew University of Jerusalem, Jerusalem, Israel

[21] Appl. No.: 713,178

[22] Filed: Mar. 18, 1985

Related U.S. Application Data

[63] Continuation-in-part of Ser. No. 572,180, Jan. 19, 1984, abandoned.

[30] Foreign Application Priority Data

Jan. 31, 1983 [IL] Israel .................................. 67789

[51] Int. Cl.$^4$ ........................................ C07F 15/00
[52] U.S. Cl. ............................................ 556/137
[58] Field of Search .................................. 556/137

[56] References Cited

U.S. PATENT DOCUMENTS 4,115,418  9/1978  Gale et al. .
4,140,707  2/1979  Cleare et al. .
4,169,846 10/1979  Kidani et al. .
4,203,912  5/1980  Hydes et al. .
4,225,529  9/1980  Hydes et al. .
4,230,631 10/1980  Hydes et al. .
4,255,347  3/1981  Kidani et al. .
4,359,425 11/1982  Totani et al. .

*Primary Examiner*—Helen M. S. Sneed
*Attorney, Agent, or Firm*—Frishauf, Holtz, Goodman & Woodward

[57] ABSTRACT

Amino-substituted-malonato platinum(II) complexes represented by the general formula $$L_2Pt^{II}(OCO)_2CH-NH_2$$

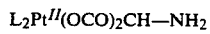

wherein L and $L_2$ are monodentate and bidentate aliphatic amine ligands respectively. Typical examples of L and $L_2$ are: $NH_3$, ethylendiamine, 1,2-diaminocyclohexane, ethylenimine, and cyclopropyl-, cyclobutyl-, cyclopentyl-, cyclohexyl-, isopropyl-, n-propyl-amine.

The compounds are characterized by high antitumor activity in mice, chemical stability and solubility in aqueous fluids for i.v. administration.

The invention provides also a preferred method for their preparation.

12 Claims, No Drawings

NOVEL ORGANOPLATINUM(II) COMPLEXES AND METHOD FOR THE PREPARATION THEREOF

This application is a continuation-in-part of application Ser. No. 572,180 filed Jan. 19, 1984, now abandoned.

BACKGROUND OF THE INVENTION

This invention relates to novel, antitumor organoplatinum complexes. More particularly, the invention relates to amino-substituted malonato platinum(II) complexes having water solubility and a high antitumor activity, and a method for their preparation.

An important requirement for an effective treatment of animal tumors with anticancer platinum complexes is still a high solubility in aqueous fluids for intravenous injection. In the last several years an extensive number of cis-dichlorodiamineplatinum (cis-DDP) analogs have been synthesized. Several of these second generation cis-DDP complexes are of general formula $L_2Pt^{II}X_2$, wherein L or $L_2$ are neutral monodentate or bidentate amine ligands respectively, and $X^-$ or $X_2^=$ are anionic monodentate or bidentate ligands respectively. In order to increase the water solubility and, therefore, the clinical potentiality of these organoplatinum compounds, several authors have suggested the use of neutral or anionic ligands having polar or hydrophilic substituents. For example, Hydes et al. (U.S. Pat. No. 4,203,912; U.S. Pat. No. 4,225,529 and U.S. Pat. No. 4,230,631) and Cleare et al. (U.S. Pat. No. 4,140,707) have reported the use of polar substituents (such as halogen, hydroxy, amino, carboxylic acid groups etc.) in the L or $L_2$ amine ligands; i.e., in the ligands which are coordinated to the platinum through a nitrogen atom. Alternatively, these inventors have reported the use of polar substituents, such as the above-cited groups, attached to the anionic ligands, but the latter being of the monodentate type, i.e., substituted-monocarboxylates. In this case, the presence of polar groups has indeed increased the water solubility of the platinum compounds. However, the use of monodentate anionic ligands, such as monocarboxylates, or of anionic ligands, such as $1/2SO_4^=$, $NO_3^-$, $OH^-$ (Gale et al., U.S. Pat. No. 4,115,418), led to kinetically reactive species, which rapidly undergo hydrolysis and, consequently, appear highly toxic in vivo (M. E. Howe-Grant and S. J. Lippard, "Metal Ions in Biological Systems", Vol. 11, page 63, Ed. H. Sigel, New York and Basel, 1980). On the other hand the use of cyclic carboxylate ions, such as oxalate, malonate or substituted malonates, has originated compounds with increased chemical stability, in addition to havine a good antitumor activity (M. J. Cleare and P. C. Hydes in "Metal Ions in Biological Systems", Vol. 11, page 1, Ed. H. Sigel, New York and Basel, 1980). The stability of these organoplatinum species has been attributed to the chelate effect of the dicarboxylato ligand, the chelate effect being maximum for a 5 or 6 membered ring as in the case of oxalate and malonate derivatives respectively. In order to increase their water solubility, Hydes et al. (U.S. Pat. No. 4,203,912; U.S. Pat. No. 4,225,529 and U.S. Pat. No. 4,230,631) and Cleare et al. (U.S. Pat. No. 4,140,707) have reported substituents attached in position 2 of the malonato ligands, but of low hydrophilicity, such as halogen, hydroxy or nitro groups. The use of a substituent of high hydrophilic character, such as a free amino group, has never been specified so far. This may be due also to the difficulty in the synthesis of such compounds.

It was conceived by the inventor to obtain structurally different malonato platinum(II) complexes, i.e., with a high hydrophilic group in position 2 of the chelating dicarboxylate, which will lead to a new class of very potent antitumor agents having chemical stability (the chelating effect of a 6 membered ring being provided by the anionic bidentate ligand), together with a high water solubility for intravenous administration.

It is, therefore, an object of the present invention to provide new malonato platinum complexes, having high antitumor properties at non-toxic doses. It is another object of the present invention to provide new malonato platinum complexes, which contain a high hydrophilic group for increased solubility in aqueous fluids for intravenous administration in the treatment of animal tumors.

Thus the invention consists in novel amino-substituted malonato platinum(II) complexes having the general formula:

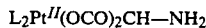

$$L_2Pt^{II}(OCO)_2CH-NH_2$$

wherein: L and $L_2$ are aliphatic amine ligands as hereinafter defined:

L is a monodentate ligand of the type $HNRR^1$ or an aminoacid, coordinated to the platinum through an N atom, such that the platinum is in the +2 oxidation state, wherein, when R=H, $R^1$ can be selected from the group consisting of hydrogen, hydroxy (e.g., hydroxylamine), substituted or unsubstituted straight- or branched-chain lower alkyl (e.g., methyl-, ethyl-, n-propyl-, isopropyl-, n-butyl-amines etc.), cycloalkyl (e.g., cyclopropyl-, cyclohexyl-amines etc.), hydroxy lower alkyl (e.g., hydroxyethyl-, hydroxypropyl-amines etc.), lower alkoxy (e.g., methoxylamine etc.), alkoxyalkylamines (e.g., methoxy-methylamine etc.), carboxylic acid (e.g., alanine etc.); R and $R^1$ can also be combined with the N atom to form an heterocyclic group (e.g., ethylenimine). It is to be understood that the organoplatinum compounds of the invention may include two identical or different monodentate amine ligands.

$L_2$ is a bidentate ligand of the type $HNR^2$—$CHR^3$—$(CR^4R^5)_n$—$CHR^6$—$NHR^7$, wherein $n=0$ or 1, and $R^2$, $R^3$, $R^4$, $R^5$, $R^6$, $R^7$ are the same or different substituents and can be selected from the group consisting of H, hydroxyl, lower alkyl (e.g., methyl, ethyl), lower alkoxy (e.g., methoxy, ethoxy), cycloalkyl (e.g., cyclohexyl); when $n=0$, $R^3$ and $R^6$ can be combined through methylene or substituted methylene groups to form a cycloalkyl group (e.g., 1,2-diaminocyclohexane); when $n=1$, $R^3$ and $R^4$ can be combined in a similar way to form a cycloalkyl group (e.g., 1-aminomethyl-2-aminocyclohexane) or $R^4$ and $R^5$ can be combined with carbon 2 of the 1,3-diaminopropane skeleton to form a cycloalkyl group (e.g., 1,1-bisaminomethyl-cyclohexane).

It is suggested that, when choosing the amine ligands (either of the monodentate or bidentate type) for the preparation of the organoplatinum complexes in accordance with this invention, the ligands should contain a limited number of alkyl or cycloalkyl substituents; that is, in order not to increase the hydrophobicity of the final compound. For example, in the case of $L=HNRR^1$, R is preferably H and $R^1$ can be selected from a lower alkyl or cycloalkyl group. Similarly, when $L_2=HNR^2$—$CHR^3$—$(CR^4R^5)_n$—$CHR^6$—$NHR^7$, $R^2$ and $R^7$ are preferably H, as also some of the $R^3$, $R^4$, $R^6$ groups.

Some typical examples of water-soluble amino-substitued malonato platinum(II) complexes included in the above general formula, without being limited thereto, are represented below:

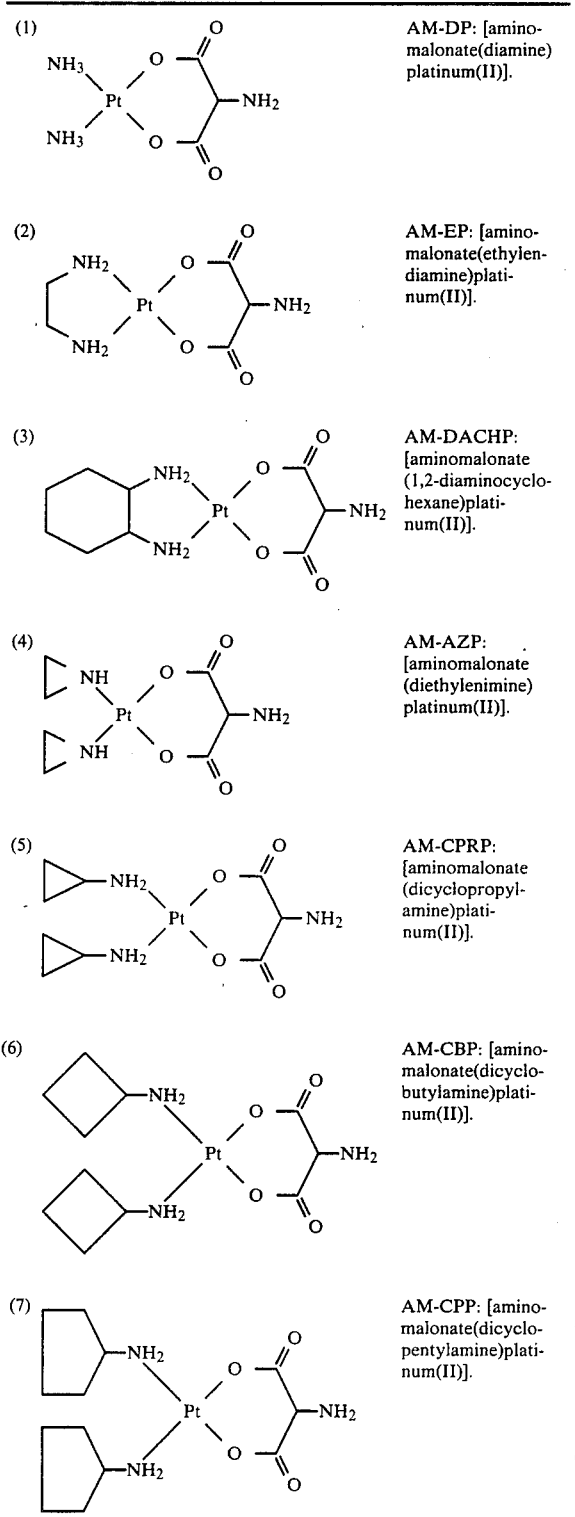

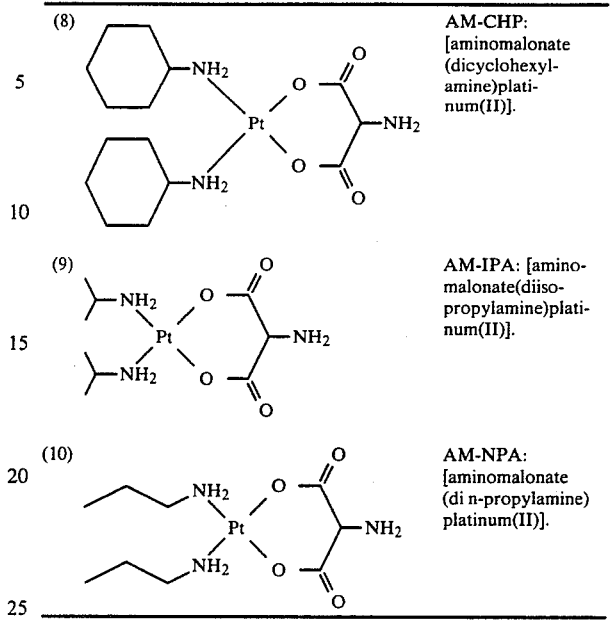

In addition to the chemical stability characteristic of platinum(II) compounds of the malonato type, the presence of a free amino group in position 2 of the malonato ligand provides a high solubility in aqueous fluids for intravenous (i.v.) administration, the solubility in water being in the range of 40 mg/ml at room temperature. Moreover, the compounds of this invention are characterized by a potent antitumor activity against malignant tumors in vivo, such as PIR-2 lymphoma, advanced L 1210 leukemia and B 16 melanoma. The experiments, hereinafter described, will illustrate the high chemotherpeutic potentiality of some representative compounds in accordance with this invention for the treatment of animal tumors. The activities are evaluated as %T/C (i.e., median survival time of treated mice divided by median survival time of untreated mice expressed as a percentage). In all the experiments, seven to ten mice were employed in a control group, and four to seven mice were employed in a test group.

ANTITUMOR ACTIVITY AGAINST PIR-2 LYMPHOMA

PIR-2 lymphoma (E. Yefenof, R. Tchakinov and E. Kedar, Cancer Immunol. Immunother., Vol. 8, page 171, 1980) is an irradiation induced tymomas and was found resistant to conventional antitumor drugs such as cyclophosphamide, CCNU or adriamicine. PIR-2 cells ($1\times10^6$ suspended in 0.5 ml of physiological saline solution) were inoculated intraperitionally (i.p.) into female C57B 1/6 mice. A dose of $1\times10^6$ cells corresponds to 100 to 1000 fold $LD_{100}$ of this tumor. Test compounds, dissolved in 5% dextrose solution, were administered i.p. as a single dose on day 1. Animals that received no drug treatment died between 17 and 19 days after inoculation of PIR-2 cells. Some of the results are given in Table 1.

TABLE 1

| Test Compound | Dose (mg/Kg) | % T/C |
|---|---|---|
| AM-DACHP | 24 | 161 |
|  | 12 | 150 |
| AM-CBP | 26 | 217 |

TABLE 1-continued

| Test Compound | Dose (mg/Kg) | % T/C |
| --- | --- | --- |
|  | 13 | 188 |
| AM-IPA | 24 | 144 |
|  | 12 | 119 |

Antitumor Activity Against L 1210 Leukemia

L 1210 leukemia in mice is generally regarded as being a highly predictive in vivo test system for indicating the clinical usefulness of a drug. L 1210 cells ($1 \times 10^6$ suspended in 0.1 ml of physiological saline solution) were inoculated i.p. into groups of $DBF_1$ F mice and into groups of $CDF_1$ F mice. The test compounds, dissolved in 5% dextrose solution were administered i.v. and/or i.p. as a single dose on day 1. Animals that received no drug treatment died between 7 and 9 days after tumor inoculation. Some of the results are given in Table 2.

TABLE 2

| Test Compound | (host: $BDF_1$ F mice) i.v. Dose (mg/Kg) | % T/C | (host: $CDF_1$ F mice) i.p. Dose (mg/Kg) | % T/C |
| --- | --- | --- | --- | --- |
| AM-DACHP | 100 | TOX | 128 | TOX |
|  | 50 | 153 | 64 | 214 |
|  | 25 | 169 | 32 | 186 |
|  | 12.5 | 159 | 16 | 136 |
| AM-CBP | — | — | 128 | 114 |
|  |  |  | 64 | 136 |
|  |  |  | 32 | 129 |

In advanced L 1210 leukemia a %T/C greater than or equal to 125 is considered a significant antitumor activity. It is apparent that the test compounds, and especially AM—DACHP, revealed an extremely high antitumor potency either when administered i.p. or i.v. and at non toxic doses.

ANTITUMOR ACTIVITY AGAINST B 16 MELANOMA

Groups of $BDF_1$ F mice were implanted i.p. with 0.5 ml of a 10% brei suspension. The test compounds, dissolved in 5% dextrose solution were administered as a daily dose for 9 days. Animals that received no drug treatment died between 20 and 21 days. Some of the results are given in Table 3.

TABLE 3

| Test compound | Dose (mg/Kg) | % T/C |
| --- | --- | --- |
| AM-DACHP | 24 | TOX |
|  | 16 | 175 |
|  | 12 | 167 |
|  | 6 | 192 |
|  | 3 | 170 |
| AM-CBP | 24 | TOX |
|  | 16 | 143 |
|  | 12 | 136 |
|  | 6 | 126 |

In B 16 melanoma a %T/C greater than or equal to 140 is considered a significant antitumor activity. Also in this malignant tumor model the test compounds have emerged as very potent anticancer agents.

According to another embodiment of the present invention it is provided a method for the preparation of the novel platinum(II) complexes. As it has been pointed out in the preamble, no platinum-malonato complex, having a free amino group as the substituent on position 2 of the malonato ligand, has been described so far. We have found that, in order to synthesize the amino-substituted malonato platinum(II) complexes of this invention, the classic method for the preparation of cis-DDP analogs is not suitable for the following reasons. The classic method, as first reported by M. J. Cleare and J. D. Hoeschele (Bioinorg. Chem., Vol. 2, page 187, 1973), and which was also described in the U.S. Pat. No. 4,115,418 by Gale et al., or in the U.S. Pat. No. 4,140,707 by Cleare et al., or in the U.S. Pat. No. 4,203,912 and U.S. Pat. No. 4,230,631 by Hydes et al., was utilized ever since for the synthesis of a great variety of platinum(II)-malonato complexes, among others. Briefly, this method is based on the treatment of the parent dihalogen-platinum(II) complex, (e.g., $L_2Pt^{II}X_2$, wherein L and $L_2$ have the meaning as given in the general formula above and $X^- =$ halogen) with a stoichiometric amount of silver nitrate or silver sulfate. The silver halogenide precipitate is removed and the supernatant solution, containing the diaquo complex, is reacted with a preformed potassium salt, or sodium salt, of malonate or substituted-malonate. In our case by using, as the starting reagent, the commerically available diethylaminomalonate hydrochloride ( $(EtOCO)_2$-CH—$NH_2$ · HCl), hydrolysis of the ester groups, in order to obtain the HCl free dicarboxylate potassium salt, will lead to unstable species, which may undergo decarboxylation. Already diethylaminomalonate is not so stable as its chloride salt. Should neutralization and hydrolysis of the malonato reagent be carried out in situ (e.g., in the presence of the diaquo complex intermediate), the liberated $Cl^{31}$ ions would react with the platinum(II) intermediate giving $L_2PtCl_2$ as a by-product. In addition to this, the inevitable raising of the pH during the hydrolysis step will lead to the formation of hydroxide-platinum species, which are known to be exceedingly inert to any further substitution.

Still another reason for the difficulty in utilizing the classic method is that, while several of the other platinum(II) malonato complexes are formed as precipitates and, therefore, can be conveniently separated and purified as known, the amine-substituted-malonato platinum(II) complexes of this invention are all water soluble; they do not form a precipitate even upon cooling the aqueous reaction mixture and, thus, cannot be easily separated from the by-products by filtration or centrifugation.

It is, therefore, another object of the present invention to provide a new and simple procedure for the synthesis of the amino-substituted-malonato platinum-(II) complexes in good yields. The commercially available diethylaminomalonate hydrochloride can still be utilized as a convenient starting material. However, aminomalonic acid or any other diester of aminomalonic acid are also satisfactory. In order to overcome the low stability of the diethylaminomalonate, diethylaminomalonate hydrochloride can be easily converted into its barium salt by direct hydrolysis of the ester groups in an aqueous solution of barium hydroxide. The barium salt of aminomalonic acid, which is stable and slightly soluble in cold water, reacts with an aqueous solution of a platinum(II) sulphate intermediate, affording the corresponding water soluble amino-substituted platinum(II) complex. After separating the insoluble $BaSO_4$, which is also formed in the reaction mixture, the desired product is recovered from the solution by evaporation of the solvent and purification with acetone. The yields in respect to the parent platinum(II) halogenide complex were up to 91%.

The overall procedure is outlined by the following scheme:

(a) 2(EtOCO)₂CH—NH₂·HCl + 3Ba(OH)₂ → 2Ba(OCO)₂CH—NH₂ ↓ + BaCl₂ + 4EtOH + 2H₂O
(b) L₂PtX₂ + Ag₂SO₄ → L₂PtSO₄ + 2AgX ↓
(c) L₂PtSO₄ + Ba(OCO)₂CH—NH₂ ↓ → L₂Pt(OCO)₂CH—NH₂ + BaSO₄ ↓ wherein: L and L₂ have the meaning as given in the general formula above; X⁻ = halogen (e.g. Cl⁻, Br⁻, J⁻).

While the invention is further illustrated in the following examples in connection with certain specific amino-substituted-malonato platinum(II) complexes, it will be understood that it is not intended to limit the invention to those particular complexes. On the contrary, it is intended to cover numerous of those complexes described by the general formula given in claim 1, alternatives, modifications or other methods for their preparation and equivalents as may be included within the scope of the invention as defined by the appended claims. Thus the following examples which include preferred embodiments will seek to illustrate the practice of this invention, it being understood that the particulars described are by way of examples and for purposes of illustrative discussion of some compounds of the present invention without being limited thereto.

In the examples, the abbreviations given for the reagents have the meaning mentioned in the specification.

EXAMPLE 1

Preparation of (NH₃)₂Pt(OCO)₂CH—NH₂, [aminomalonate(diamine)platinum(II)], AM—DP A suspension of 1 g of cis—(NH₃)₂PtI₂ in 15 ml of water, containing 0.61 g of silver sulfate was stirred for 0.5 hrs at 50° C. The silver iodide precipitate was separated and the filtrate pipetted to 0.65 g of Ba(OCO)₂CH—NH₂, suspended in 10 ml of water. The reaction mixture was stirred at 25° C. for 2 hrs, cooled on ice and filtered, washing the residue with icy water. The clear filtrate was partially concentrated to about 2 ml. Addition of ethanol afforded a white precipitate, which was filtered out, washed with acetone and dried in vacuo. By this work-up the product was monohydrate. Yield 75%.

Analysis—Calculated for C₃H₉N₃O₄Pt·H₂O: C = 9.89; H = 3.05; N = 11.53. Found: C = 9.90; H = 2.91; N = 11.47.

EXAMPLE 2

Preparation of C₂H₄(NH₂)₂Pt(OCO)₂CH—NH₂, [aminomalonate (ethylenediamine)-platinum(II)], AM—EP.

Analogously to Example 1, aminomalonate(ethylenediamine)platinum(II) was obtained as the monohydrate in 89% yield from 1 g of (ethylenediamine)-platinum diiodide, 0.58 g of silver sulfate and 1 g of Ba(OCO)₂CH—NH₂.

Analysis—Calculated for C₅H₁₁N₃O₄·H₂O: C = 15.38; H = 3.36; N = 10.76. Found: C = 15.54; H = 3.24; N = 10.34.

EXAMPLE 3

Preparation of C₆H₁₀(NH₂)₂Pt(OCO)₂CH—NH₂, [aminomalonate(1,2-diaminocyclohexane)platinum(II)], AM—DACHP Analogously to Example 1, aminomalonate(1,2-diaminocyclohexane)-platinum(II) was obtained as the monohydrate in 88% yield from 1 g of (1,2-diaminocyclohexane)platinum diiodide, 0.53 g of silver sulfate and 1 g of Ba(OCO)₂CH—NH₂.

Analysis—Calculated for C₉H₁₇N₃O₄Pt·H₂O: C = 24.31; H = 4.32. Found: C = 24.26; H = 4.42.

EXAMPLE 4

Preparation of (C₂H₄NH)₂Pt(OCO)₂CH—NH₂, [aminomalonate(diethylenimine)platinum(II)], AM—AZP Analogously to Example 1, aminomalonate(diethylenimine)platinum(II) was obtained as the monohydrate in 53% yield from cis-(diethylenimine)-platinum diiodide, 0.55 g of silver sulfate and 0.95 g of Ba(OCO)₂CH—NH₂.

Analysis—Calculated for C₇H₁₃N₃O₄Pt·H₂O: C = 20.18; H = 3.64; N = 10.09. Found: C = 20.07; H = 3.48; N = 9.81.

EXAMPLE 5

Preparation of (C₃H₅NH₂)₂Pt(OCO)₂CH—NH₂, [aminomalonate(dicyclopropylamine)platinum(II)], AM—CPRP.

Analogously to Example 1, aminomalonate(dicyclopropylamine)platinum(II) was obtained in 67% yield from 1 g of cis-(dicyclopropylamine)platinum diiodide, 0.53 g of silver sulfate and 0.9 g of Ba(OCO)₂CH—NH₂.

Analysis—Calculated for C₉H₁₇N₃O₄Pt: C = 25.34; H = 4.03; N = 9.85. Found: C = 25.13; H = 3.93; N = 9.98.

EXAMPLE 6

Preparation of (C₄H₇NH₂)₂Pt(OCO)₂CH—NH₂, [aminomalonate(dicyclobutylamine)platinum(II)], AM—CBP Analogously to Example 1, aminomalonate(dicyclobutylamine)platinum(II) was obtained as the dihydrate in 65% yield from 1 g of cis-(dicyclobutylamine)-platinum diiodide, 0.50 of silver sulfate and 0.72 g of Ba(OCO)₂CH—NH₂.

Analysis—Calculated for C₁₁H₂₁N₃O₄Pt·2H₂O: C = 26.92; H = 5.14; N = 8.56. Found: C = 27.15; H = 5.00; N = 8.12.

EXAMPLE 7

Preparation of (C₅H₉NH₂)₂Pt(OCO)₂CH—NH₂, [aminomalonate(dicyclopentylamine)platinum(II)], AM—CPP Analogously to Example 1, aminomalonate(dicyclopentylamine)platinum(II) was obtained in 82% yield from 1 g of cis-(dicyclopentylamine)platinum diiodide, 0.48 g of silver sulfate and 0.69 g of Ba(OCO)₂CH—NH₂.

Analysis—Calculated for C₁₃H₂₅N₃O₄Pt: C = 32.34; H = 5.23; N = 8.71. Found: C = 32.13; H = 5.47; N = 8.65.

EXAMPLE 8

Preparation of (C₆H₁₁NH₂)₂Pt(OCO)₂CH—NH₂, [aminomalonate(dicyclohexylamine)platinum(II)], AM—CHP Analogously to Example 1, aminomalonate(dicyclohexylamine)platinum(II) was obtained as the monohydrate in 42% yield from 1 g of cis-(dicyclohexylamine)platinum diiodide, 0.46 g of silver sulfate and 0.47 g of Ba(OCO)₂CH—NH₂.

Analysis—Calculated for $C_{15}H_{29}N_3O_4Pt \cdot H_2O$: C=34.10; H=5.92; N=7.95. Found: C=34.13; H=5.90; N=7.79.

EXAMPLE 9

Preparation of $[(CH_3)_2CH-NH_2]_2Pt(OCO)_2CH-NH_2$, [aminomalonate(diisopropylamine)platinum(II)], AM—IPA Analogously to Example 1, aminomalonate(diisopropylamine)platinum(II) was obtained as the monohydrate in 81% yield from 1 g of cis-(diisopropylamine)-platinum diiodide, 0.52 g of silver sulfate and 0.54 g of $Ba(OCO)_2CH-NH_2$.

Analysis—Calculated for $C_9H_{21}N_3O_4Pt \cdot H_2O$: C=24.10; H=5.18; N=9.37. Found: C=23.86; H=5.28; N=9.21.

EXAMPLE 10

Preparation of $[CH_3(CH_2)_2NH_2]_2Pt(OCO)_2CH-NH_2$, [aminomalonate(dinpropylamine)platinum(II)], AM—NPA Analogously to Example 1, aminomalonate(din-propylamine)platinum(II) was obtained in 91% yield from 1 g of cis-(din-propylamine)platinum diiodide, 0.52 g of silver sulfate and 0.54 g of $Ba(OCO)_2CH-NH_2$.

Analysis—Calculated for $C_9H_{21}N_3O_4Pt$: C=25.10; H=4.93; N=9.76. Found: C=25.15; H=5.23; N=9.29.

We claim:

1. Amino-substituted malonato platinum complexes having the general formula:

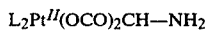

wherein:
L is a monodentate aliphatic amine ligand of the type $HNRR^1$ or an amino acid, wherein, when R=H, $R^1$ is selected from the group consisting of H, hydroxy, lower alkyl, cycloalkyl, hydroxy lower alkyl, and lower alkoxy; R and $R^1$ can also be combined to form an imine group;

$L_2$ is a bidentate aliphatic amine ligand of the type $HNR^2-CHR^3-(CR^4R^5)_n-CHR^6-NHR^7$, wherein n=0 or 1, and $R^2$, $R^3$, $R^4$, $R^5$, $R^6$, $R^7$ are the same or different substituents and are selected from the group consisting of H, hydroxy, lower alkyl, lower alkoxy cycloalkyl; when n=0, $R^3$ and $R^6$ can be combined to form a cycloalkyl group; when n=1, $R^3$ can be combined with $R^4$, or $R^4$ and $R^5$ can be combined with the carbon atom, to form in each case a cycloalkyl group.

2. Aminomalonate(diamine)platinum(II), (AM—DP) of the formula of claim 1, wherein L is $NH_3$.

3. Aminomalonate(ethylendiamine)platinum(II), (AM—EP), of the formula of claim 1, wherein $L_2$ is ethylendiamine.

4. Aminomalonate(1,2-diaminocyclohexane)-platinum(II), (AM—DACHP), of the formula of claim 1, wherein $L_2$ is 1,2-diaminocyclohexane.

5. Aminomalonate(diethylenimine)platinum(II), (AM—AZP), of the formula of claim 1, wherein L is ethylenimine.

6. Aminomalonate(dicyclopropylamine)platinum(II), (AM—CPRP), of the formula of claim 1, wherein L is cyclopropylamine.

7. Aminomalonate(dicyclobutylamine)platinum(II), (AM—CBP), of the formula of claim 1, wherein L is cyclobutylamine.

8. Aminomalonate(dicyclopentylamine)platinum(II), (AM—CPP), of the formula of claim 1, wherein L is cyclopentylamine.

9. Aminomalonate(dicyclohexylamine)platinum(II), (AM—CHP), of the formula of claim 1, wherein L is cyclohexylamine.

10. Aminomalonate(diisopropylamine)platinum(II), (AM—IPA), of the formula of claim 1, wherein L is isopropylamine.

11. Aminomalonate(din-propylamine)platinum(II), (AM—NPA), of the formula of claim 1, wherein L is n-propylamine.

12. A method for the preparation of amino-substituted malonato platinum complexes having the general formula:

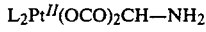

wherein:
L is a monodentate aliphatic amine ligand of the type $HNRR^1$ or an aminoacid, wherein, when R=H, $R^1$ is selected from the group consisting of H, hydroxy, lower alkyl, cycloalkyl, hydroxy lower alkyl, and lower alkoxy; R and $R^1$ can also be combined to form an imine group;

$L_2$ is a bidentate aliphatic amine ligand of the type $HNR^2-CHR^3-(CR^4R^5)_n-CHR^6-NHR^7$, wherein n=0 or 1, and $R^2$, $R^3$, $R^4$, $R^5$, $R^6$, $R^7$ are the same or different substituents and are selected from the group consisting of H, hydroxy, lower alkyl, lower alkoxy, cycloalkyl; when n=0, $R^3$ and $R^6$ can be combined to form a cycloalkyl group; when n=1, $R^3$ can be combined with $R^4$, or $R^4$ and $R^5$ can be combined with the carbon atom, to form in each case a cycloalkyl group;

said method comprising reacting the barium salt of aminomalonic acid with a platinum(II) sulfate intermediate having the general formula $L_2PtSO_4$, wherein L and $L_2$ are defined as in the general formula above, to form the complex of the formula $L_2Pt^{II}(OCO)_2CH-NH_2$.

* * * * *